United States Patent
Wang et al.

(10) Patent No.: US 11,213,557 B2
(45) Date of Patent: Jan. 4, 2022

(54) LACTOBACILLUS PLANTARUM CCFM1019, FERMENTED FOODS THEREOF, AND APPLICATION THEREOF IN PREPARATION OF MEDICINE FOR PROMOTING EXCRETION OF PLASTICIZERS AND METABOLITES THEREOF FROM BODY

(71) Applicant: Jiangnan University, Wuxi (CN)

(72) Inventors: Gang Wang, Wuxi (CN); Wei Chen, Wuxi (CN); Qian Chen, Wuxi (CN); Jianxin Zhao, Wuxi (CN); Hao Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/019,900

(22) Filed: Sep. 14, 2020

(65) Prior Publication Data
US 2020/0405790 A1  Dec. 31, 2020

Related U.S. Application Data

(63) Continuation of application No. PCT/CN2018/079154, filed on Mar. 15, 2018.

(51) Int. Cl.
| | | |
|---|---|---|
| *A61K 35/747* | (2015.01) | |
| *A61K 35/00* | (2006.01) | |
| *A23L 29/00* | (2016.01) | |
| *C12R 1/25* | (2006.01) | |

(52) U.S. Cl.
CPC .......... *A61K 35/747* (2013.01); *A23L 29/065* (2016.08); *A61K 2035/115* (2013.01); *C12R 2001/25* (2021.05)

(58) Field of Classification Search
None
See application file for complete search history.

(56) References Cited

FOREIGN PATENT DOCUMENTS

| CN | 107523514 A | | 12/2017 |
|---|---|---|---|
| CN | 108384735 A | * | 3/2018 |
| WO | WO 2019174003 A1 | * | 9/2019 |

* cited by examiner

*Primary Examiner* — Sarvamangala Devi
(74) *Attorney, Agent, or Firm* — IPro, PLLC; Na Xu

(57) ABSTRACT

The disclosure herein discloses *L. plantarum* CCFM1019, fermented foods thereof, and application thereof in preparation of a medicine for promoting excretion of plasticizers and metabolites thereof from the body. The *L. plantarum* CCFM1019 not only is significantly better than the intestinal resident bacteria *E. coli* and *E. faecalis* in terms of the effect of promoting the excretion of DEHP and MEHP, but also is better than the commercial strain *L. rhamnosus* LGG. Therefore, the *L. plantarum* CCFM1019 of the disclosure can be used as an effective means to prevent and alleviate body damage caused by DEHP and MEHP, and has no toxic side effects of drugs. *L. plantarum* CCFM1019 can be used to prepare pharmaceutical compositions and fermented foods for alleviating and preventing the toxicity of DEHP and metabolites thereof, and has a very broad application prospect.

8 Claims, 4 Drawing Sheets

LACTOBACILLUS PLANTARUM CCFM1019, FERMENTED FOODS THEREOF, AND APPLICATION THEREOF IN PREPARATION OF MEDICINE FOR PROMOTING EXCRETION OF PLASTICIZERS AND METABOLITES THEREOF FROM BODY

TECHNICAL FIELD

The disclosure herein belongs to the technical field of microorganism, and in particular relates to *Lactobacillus plantarum* CCFM1019, fermented foods thereof, and application thereof in preparation of a medicine for promoting excretion of plasticizers and metabolites thereof from the body.

BACKGROUND

As a plasticizer, bis(2-ethyl hexyl) phthalate (hereinafter referred to as DEHP) is added to plastics to increase flexibility and plasticity. Due to low price, DEHP is widely used in the production of plastic products such as medical instruments and chemical products, and is currently the most widely used plasticizer in China. In the plastic products, DEHP is mainly combined with other molecules in the form of hydrogen bonds and van der Waals force rather than covalent bonds. Therefore, DEHP is very easy to escape during use, and then migrate into the environment and even the human body, causing harm to animals, plants and human health.

Studies have shown that the absorption and distribution period of DEHP in the human body lasts for about 4-8 h, and most of the DEHP can be completely metabolized by the human body within 24 h. Urine is the main route of excretion of DEHP. 24 h after DEHP enters the human body, less than 10% of the DEHP stock solution is directly excreted in urine, and about 67% of the DEHP is converted into five secondary metabolites and excreted in urine. Because DEHP is fat-soluble, a small amount of DEHP is retained in fat or milk. DEHP stored in adipose tissue cannot be completely metabolized for a long time, and has a half-life of 156 h.

The toxic effect of DEHP on the body is mainly exerted by the metabolite mono(2-ethyl hexyl) phthalate (MEHP). DEHP and the metabolite MEHP thereof accumulated in the body can produce a variety of toxicity, including reproductive toxicity, liver toxicity, embryo toxicity, thyroid toxicity, neurotoxicity, and the like. As a peroxisome proliferator, DEHP can break the redox equilibrium in a cell and increase the level of free radicals such as ROS in the cell. In addition, DEHP and metabolites thereof can also affect the expression of antioxidant genes and lead to accumulation of ROS, thus triggering lipid peroxidation, producing lipid peroxides such as malondialdehyde, and causing oxidative damage. At present, the damage of DEHP to the human body is prevented and alleviated mainly through taking some antioxidant bioactive substances such as vitamin C, vitamin E, grape seed extract, and flavonoids. However, to alleviate the toxic effects of DEHP by supplementing active substances, a large dose is required, but excessive intake of the active substances can also cause side effects on the body. For example, excessive intake of flavonoids can cause secretion disorders in the human body. Moreover, the above method cannot reduce the intake and residue of the plasticizer in the body. Therefore, it is particularly necessary to find a new and safe prevention and treatment method.

In the currently published literature, there is no patent for alleviating the toxicity of the plasticizer through probiotics. According to existing literature reports, the highest adsorption rate of probiotics to DEHP in vitro is only 9.62%, and the adsorption effect is not ideal. Therefore, it is particularly important to develop a probiotic with strong adsorption capacity for the plasticizer, and prove through animal experiments that the probiotic has a good effect on alleviating the toxic damage of the plasticizer in the body.

SUMMARY

The disclosure provides *L. plantarum* CCFM1019, deposited on Feb. 11, 2018 at the Guangdong Microbial Culture Collection Center, Guangdong Institute of Microbiology, 5th Floor, Building 59, Yard 100, Xianlie Middle Road, Guangzhou, with an accession number of GDMCC No. 60333.

The disclosure further provides a microbial preparation, containing the *L. plantarum* CCFM1019.

In one embodiment, the microbial preparation is a culture solution prepared by fermentation of *L. plantarum* CCFM1019 in an MRS medium.

In one embodiment, after *L. plantarum* CCFM1019 is fermented in an MRS medium, bacterial cells are collected and mixed with a cytoprotective agent, and then the mixture is subjected to freeze-drying treatment to obtain a freeze-dried preparation containing viable cells of the *L. plantarum* CCFM1019.

In one embodiment, the microbial preparation is a bacterial suspension of *L. plantarum* CCFM1019.

The disclosure further provides application of *L. plantarum* CCFM1019 in preparation of products capable of promoting excretion of plasticizers and metabolites thereof from mammals.

In one embodiment, the plasticizers comprise bis(2-ethyl hexyl) phthalate and mono(2-ethyl hexyl) phthalate.

In one embodiment, the fermented food can be resistant to gastric acid and bile salts, promote excretion of plasticizers and metabolites thereof from the body, reduce the content of the plasticizers and the metabolites thereof in serum, and significantly reduce the damage of the plasticizers and the metabolites thereof to testicular tissue and liver tissue.

The disclosure has the beneficial effects as follows: the *L. plantarum* CCFM1019 has good resistance to gastric acid and bile salts, can promote excretion of the plasticizer DEHP and the metabolite MEHP thereof from the body, reduces the content of the plasticizer and the metabolite thereof in serum, and significantly reduces the damage of the plasticizer and the metabolite thereof to testicular tissue and liver tissue.

The *L. plantarum* CCFM1019 not only is significantly better than the intestinal resident bacteria *Escherichia coli* (DEHP: 5.86%, MEHP: 0.28%) and *Enterococcus faecalis* (DEHP: 1.75%, MEHP: 0.17%) in terms of in vitro adsorption of DEHP and MEHP (52.22% and 70.54% respectively), but also is better than the commercial strain *Lactobacillus rhamnosus* LGG (DEHP: 13.75%, MEHP: 15.60%). In the bodies of rats, *L. plantarum* CCFM1019 can significantly reduce the DEHP and MEHP content in serum (by 54.3% and 55.7% respectively compared to the blank control group), and at the same time increase the DEHP and MEHP content in feces (by 34.18% and 93.88% respectively compared to the blank control group). Therefore, the *L. plantarum* CCFM1019 of the disclosure can be used as an effective means to prevent and alleviate body damage caused by DEHP and MEHP, and has no toxic side effects of drugs. The *L. plantarum* CCFM1019 can be used to prepare pharmaceutical compositions and fermented foods for alleviating and preventing the toxicity of DEHP and the metabolites thereof, and has a very broad application prospect.

Deposit of Biological Materials

The *Lactobacillus plantarum* CCFM1019 was deposited on Feb. 11, 2018 at the Guangdong Microbial Culture Collection Center, Guangdong Institute of Microbiology, 5th Floor, Building 59, Yard 100, Xianlie Middle Road, Guangzhou, with an accession number GDMCC No. 60333.

DETAILED DESCRIPTION

Figure 1:
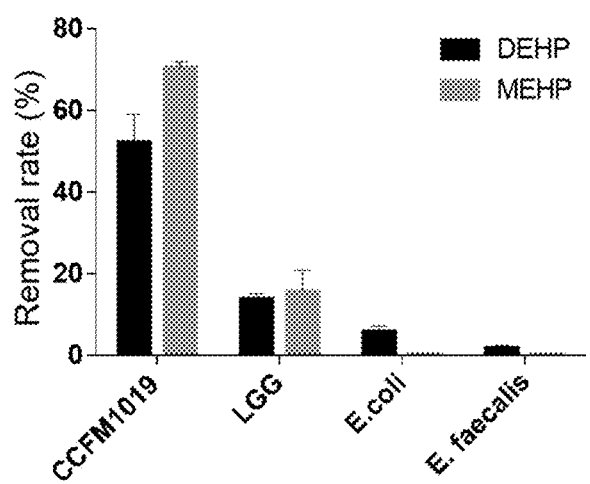
FIG. 1 is a schematic diagram showing comparison in adsorption capacity to DEHP and MEHP in vitro of a strain of the present application and control strains *Lactobacillus rhamnosus* GG (LGG), *Escherichia coli* and *Enterococcus faecalis*.

The *L. plantarum* CCFM1019 of the disclosure was deposited on Feb. 11, 2018 at the Guangdong Microbial Culture Collection Center, Guangdong Institute of Microbiology, 5th Floor, Building 59, Yard 100, Xianlie Middle Road, Guangzhou, with an accession number GDMCC No. 60333.

The *L. plantarum* CCFM1019 has the Following Biological Characteristics:

(1) Bacterial characteristics: The bacterium is Gram-positive, has acid resistance, grows well under pH 3.0-7.2 environmental conditions, and does not form spores. The bacteria is about (0.9-1.2) μm×(3.0-8.0) μm, is baculiform with rounded ends, appears individually, in pairs or as short chains, usually lacks flagella but can move.

(2) Colony characteristics: Obvious colonies are formed on an MRS medium, are 0.3-3.0 mm in diameter, round, convex or lenticular, dense, and white, have smooth to mucus-like soft surfaces, and do not form mycelia.

(3) Growth properties: The bacterium is a facultative anaerobic bacterium, the optimum growth temperature is 36-38° C., the growth is good at 32-38° C., and the bacterium can grow at 15° C. The optimum initial pH is 6-7. The bacterium grows well in a culture solution containing glucose.

(4) The bacterium has good tolerance to artificial simulated gastrointestinal fluid.

(5) The bacterium can alleviate the damage of DEHP and the metabolite MEHP to the testis.

(6) The bacterium can significantly increase the levels of DEHP and MEHP in feces.

(7) The bacterium can significantly reduce the levels of DEHP and MEHP in serum, and reduce the accumulation of DEHP and MEHP in the body.

(8) The bacterium can significantly improve the levels of glutamic-pyruvic transaminase (ALT), glutamic oxalacetic transaminase (AST) and alkaline phosphatase (ALP) in serum.

Extraction Method of Strain:

(I) Isolation and screening of lactic acid bacteria, including the following steps:

(1) collecting pickle samples from different regions and enriching the samples in MRS media containing sorbitol for 12 h;

(2) performing gradient dilution of the enriched samples, spreading the samples subjected to gradient dilution on MRS solid plates supplemented with 0.02% bromcresol purple, and performing culturing for 24-48 h;

(3) selecting single colonies with obvious color-changing zones and conforming to the basic morphology of lactic acid bacteria, performing plate streaking purification, and screening and isolating lactic acid bacteria;

(4) culturing the above single colonies in liquid MRS culture solutions for 24 h, then performing Gram staining, and selecting Gram-positive bacteria for performing subsequent experiments.

(II) Preliminary identification of *L. plantarum*: Calcium-dissolving zone determination method:

(1) culturing the lactic acid bacteria screened in step (I) in a liquid sorbitol MRS culture solution for culturing the lactic acid bacteria for 24 h, then taking 1 mL of the culture and centrifuging the culture at 8000×g for 2 min;

(2) performing washing twice with a 0.05 M $KH_2PO_4$ solution;

(3) resuspending the obtained bacterial sludge, streaking the bacterial sludge on a sorbitol MRS-0.75% $CaCO_3$ solid culture medium, and culturing for 24 h;

(4) selecting colonies with obvious calcium-dissolving zones and being convex-round, fine and white without mycelia, and after Gram staining, preliminarily judging the bacteria as *Lactobacillus* if the bacterial cells are bacilliform as observed under microscope.

(III) Molecular biological identification of *L. plantarum*

(1) performing extraction of a genome of single bacteria:

A. culturing the lactic acid bacteria screened in step (II) overnight, putting 1 mL of the bacterial suspension cultured overnight in a 1.5 mL centrifuge tube, centrifuging the bacterial suspension at 10000×g for 2 min, and discarding the supernatant to obtain bacterial cells;

B. after purging the bacterial cells with 1 mL of sterile water, centrifuging the bacterial cells at 10000×g for 2 min, and discarding the supernatant to obtain the bacterial cells;

C. adding 200 μL of SDS lysate and performing water bath at 80° C. for 30 min;

D. adding 200 μL of phenol-chloroform solution to the bacterial cell lysate, wherein the composition in volume ratio of the phenol-chloroform solution is Tris saturated phenol:chloroform:isoamyl alcohol=25:24:1; after mixing by inversion, performing centrifuging at 12000×g for 5-10 min, and taking 200 μL of supernatant;

E. adding 400 μL of ice alcohol or ice isopropanol to the 200 μL of supernatant, allowing the mixed solution to stand for 1 h at −20° C., performing centrifuging at 12000×g for 5-10 min, and discarding the supernatant;

F. adding 500 μL of 70% (volume percentage) ice alcohol to resuspend the precipitate, performing centrifuging at 12000×g for 1-3 min, and discarding the supernatant;

G. drying the precipitate in an oven at 60° C., or drying the precipitate naturally;

H. re-dissolving the precipitate with 50 μL of $ddH_2O$ for PCR;

(2) performing 16S rDNA PCR:

A. bacterial 16S rDNA 50 µL PCR reaction system:
10×Taq buffer, 5 µL; dNTP, 5 µL; 27 F, 0.5 µL; 1492R, 0.5 µL; Taq enzyme, 0.5 µL; template, 0.5 µL; ddH$_2$O, 38 µL.

B. PCR conditions:
95° C. 5 min; 95° C. 10 s; 55° C. 30 s; 72° C. 30 s; step 2-4 30×; 72° C. 5 min; 12° C. 2 min;

(3) preparing a 1% agarose gel, then mixing the PCR product with 10× loading buffer, performing loading at a loading amount of 5 µL, performing running at 120 V for 30 min, and then performing gel imaging;

(4) performing sequencing analysis on the PCR product of 16S rDNA, using BLAST to search in GeneBank and compare the similarity with the sequence results, selecting a new *Lactobacillus* strain with the sequencing result identified as belonging to *Lactococcus lactis*, and storing the new *Lactobacillus* strain at −80° C. for later use.

Example 1: Tolerance of *L. plantarum* CCFM1019 to Simulated Gastrointestinal Fluid Cryopreserved *L. plantarum* CCFM1019 was inoculated by streaking in an MRS solid culture medium and cultured statically and aerobically for 24 h at a temperature of 37° C. After subculturing 2-3 times in a liquid culture solution, the *L. plantarum* CCFM1019 culture solution was taken and centrifuged at 8000×g for 5 min, and bacterial cells were collected. The bacterial cells were resuspended (1:1) in artificial simulated gastric juice with the pH of 2.5 (an MRS medium containing 1% pepsin, pH=2.5), and the solution was mixed and then aerobically cultured at 37° C. Samples were taken at the beginning (0 h), 1 h, 2 h and 3 h respectively. Plate colony counting was performed by pouring culture using an MRS agar culture medium, the number of viable bacteria was determined, and the survival rate was calculated. The survival rate is the ratio of the number of viable bacteria in the culture solution to the number of viable bacteria at 0 h, expressed in %.

The *L. plantarum* CCFM1019 culture solution was taken and centrifuged at 8000×g for 5 min, and bacterial cells were collected. The bacterial cells were resuspended (1:1) in artificial simulated intestinal juice (an MRS medium containing 0.3% bovine bile salt and 1% trypsin, pH=8.0), and then aerobically cultured at 37° C. Samples were taken at the beginning (0 h), 1 h, 2 h, 3 h and 4 h respectively. Plate colony counting was performed by pouring culture using MRS agar culture medium, the number of viable bacteria was determined, and the survival rate was calculated. The survival rate is the ratio of the number of viable bacteria during sampling in the culture solution to the number of viable bacteria at 0 h, expressed in %. The experimental results are shown in Table 1 and Table 2. It can be seen that *L. plantarum* CCFM1019 has good tolerance to artificial gastric juice and intestinal juice.

TABLE 1

Tolerance of *L. plantarum* CCFM1019 in artificial simulated gastric juice

| | Artificial simulated gastric juice | | |
|---|---|---|---|
| Treatment time (h) | 1 | 2 | 3 |
| Survival rate (%) | 96.42 ± 2.23 | 95.52 ± 3.13 | 92.55 ± 3.77 |

TABLE 2

Tolerance of *L. plantarum* CCFM1019 in artificial simulated intestinal juice

| | Artificial simulated intestinal juice | | | |
|---|---|---|---|---|
| Treatment time (h) | 1 | 2 | 3 | 4 |
| Survival rate (%) | 91.75 ± 5.23 | 80.22 ± 6.67 | 70.33 ± 5.24 | 60.98 ± 6.07 |

Example 2: Adsorption Capacity of *L. plantarum* CCFM1019 to DEHP and MEHP in Aqueous Solution Containing Plasticizer DEHP or MEHP In Vitro Adsorption of bacterial cells: After purification and activation culture of experimental bacteria, the bacteria were inoculated into MRS liquid culture media according to an inoculum concentration of 1% (v/v), and cultured at 37° C. for 20 h (*E. coli* was cultured in an LB culture medium at 37° C. with shaking; *E. faecalis* was cultured at 37° C. in an MRS liquid culture medium). Then the culture solutions were centrifuged at 8000×g for 20 min, and the supernatants were discarded. After resuspension with ultrapure water, centrifugation was performed at 8000×g for 20 min, and the supernatants were discarded to obtain viable bacterial cells, namely wet bacterial cells. The wet bacterial cells were resuspended in a 50 mg/L DEHP or 10 mg/L MEHP aqueous solution, and the final bacterial cell concentration reached 1 g wet bacterial cells/L. As a blank control, wet bacterial cells were resuspended in ultrapure water without DEHP and MEHP. The volume of each group is 1 mL. The mixed solutions were incubated with shaking at 37° C. for 4 h, and then centrifugation was performed at 3500×g for 10 min. After the supernatants were collected and passed through a 0.22 µm filter membrane, the content of DEHP or MEHP in the filtrate was determined by UPLC-MS, and the average value of 3 parallel experiments is taken.

Determination of DEHP and MEHP adsorption capacity: The content of remaining DEHP or MEHP in filtrates was determined by UPLC-MS of Waters EYNAPT MS system, a C18 column (2.1×100 mm, 1.7 µm, Waters Co.) was used, the column temperature was 35° C., and the injection volume was 1 µL. Eluents A and B were 100% methanol and 0.1% (v/v) formic acid aqueous solution respectively, gradient elution was used, and the flow rate is 0.3 mL/min. The gradient elution conditions are shown in Table 3.

TABLE 3

Gradient elution conditions

| t/min | 0-0.5 | 0.5-7.0 | 7.0-7.5 | 7.5-10.0 |
|---|---|---|---|---|
| Proportion of eluent A | 60% | 60-100% | 100-60% | 60% |

Mass spectrometry conditions: The ionization source was an ESI source; MRM detection (DEHP: MS+; MEHP: MS−) was used; the Capillary was 3.0 KV; the Conc was 40.00 V; the Source Temperature was 120° C.; the desolvation temperature was 400° C.; the Conc Gas Flow was 50 L/h; and the Desolvation Gas Flow was 700 L/h. The gas flow rate was 0.1 mL/min; the mass-to-charge ratio scanning range was 100-2000; the scanning time was 1 s, and the interval was 0.061 s. The results were analyzed by MassLynxV4.1 (Waters Co.). In this study, the minimum detection limits of DEHP and MEHP were 0.05 ppm and 0.1 ppm, respectively. The adsorption rate of lactic acid bacteria was calculated based on the difference in the DEHP or MEHP concentration before and after adsorption, and the adsorption rate was calculated by the following formula:

Adsorption rate (%)=[(The content of plasticizer in an aqueous solution before adsorption−the content of plasticizer in ultrapure water)−(The content of plasticizer in a supernatant after adsorption−the content of plasticizer in a supernatant in the blank control)]/(The content of plasticizer in an aqueous solution before adsorption−the content of plasticizer in ultrapure water)×100.

The determination results are shown in FIG. 1. It is obvious from FIG. 1 that compared with a commercial bacterium LGG (DEHP: 13.75%, MEHP: 15.60%) and intestinal resident bacteria *E. coli* (DEHP: 5.86%, MEHP: 0.28%) and *E. faecalis* (DEHP: 1.75, MEHP: 0.17%), the adsorption rates (DEHP: 52.22%, MEHP: 70.54%) of the *L. plantarum* CCFM1019 of the disclosure are significantly higher than those of the control bacteria, and far higher than the previously reported adsorption rate of 9.62% of DEHP. Therefore, the *L. plantarum* CCFM1019 has good adsorption capacity to DEHP and MEHP.

Example 3: Toxic Side Effects of *L. plantarum* CCFM1019 on SD

The *L. plantarum* CCFM1019 was resuspended in a 2% (w/v) sucrose solution with a bacterial cell density of $1.0 \times 10^9$ CFU/mL. 10 healthy male SD rats weighing about 100 g were taken, given 2 mL of suspension of the above concentration through gavage daily, observed for a week, and recorded for the death and body weight.

The experimental results are listed in Table 4. The results showed that feeding *L. plantarum* CCFM1019 with a concentration of $1.0 \times 10^9$ CFU/mL had no significant effects on the rats, and the rats had no significant change in the body weight or death. The rat had no obvious pathological symptoms in appearance.

Figure 2:
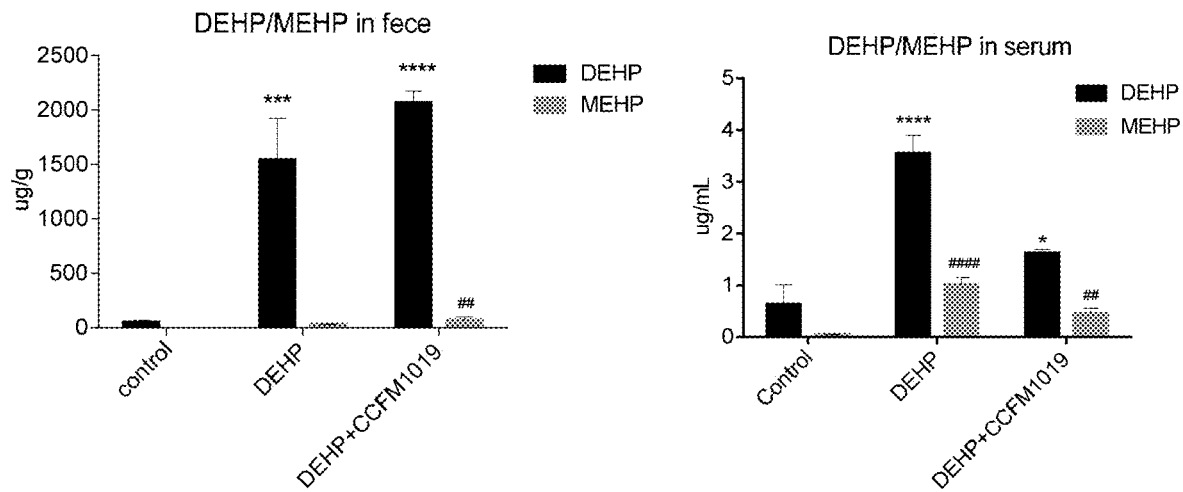
FIG. 2 is a schematic diagram showing influence of the strain of the present application on DEHP and MEHP content in serum and feces.

Example 4: Influence of *L. plantarum* CCFM1019 on DEHP and MEHP Content in Serum and Feces of DEHP-Exposed Rats 18 healthy male SD rats weighing about 100 g were randomly divided into 3 groups: a blank control group (control), a DEHP exposure model group (DEHP), and a *L. plantarum* CCFM1019 intervention group (DEHP+CCFM1018), and there were 6 rats in each group. On days 1-7 of the experiment, the blank control group and the DEHP exposure model group were given 2 mL of 2% (w/v) sucrose solution through gavage daily, and the rats in the *L. plantarum* CCFM1019 intervention group were fed with 2 mL of the *L. plantarum* CCFM1019 suspension with a concentration of $1.0 \times 10^9$ CFU/mL prepared according to Example 3 of this specification. On day 8, the drinking water of the blank control group was changed to an aqueous solution containing 0.05% (m/V) sucrose fatty acid ester. DEHP was dissolved in the 0.05% (m/V) sucrose fatty acid ester aqueous solution, and except the blank group, the drinking water was exposed to the toxicant at a dose of 3000 mg/kg body weight every day. Gavage with the probiotic and the control 2% (w/v) sucrose solution continued during the exposure period. After four weeks of continuous exposure, the feces were collected and the animals were euthanized. Testes and serum were collected, and the DEHP and MEHP content in the serum and feces were determined. The results of the determination are shown in FIG. 2. In the figure, * indicates significance compared to the DEHP content in the control group; *P<0.05, P<0.01, *P<0.005, ****P<0.001; #P<0.05, ##P<0.01, ###P<0.005, ####P<0.001.

Experimental results showed that after intervention of the *L. plantarum* CCFM1019, the DEHP and MEHP content in serum was significantly reduced (by 54.3% and 55.7% respectively compared to the blank control group), and at the same time the DEHP and MEHP content in feces was increased (by 34.18% and 93.88% respectively compared to the blank control group). This indicates that the *L. plantarum* CCFM1019 can effectively promote the excretion of DEHP and the metabolite MEHP from the body.

Figure 3:
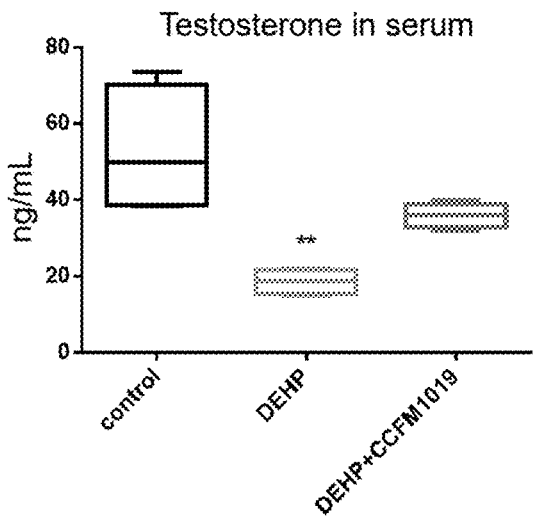
FIG. 3 is a schematic diagram showing improvement of the strain of the present application on level of testosterone in serum of a DEHP exposure model rat.

Example 5: Alleviating Effect of *L. plantarum* CCFM1019 on Reproductive Toxicity of DEHP-Exposed Rats The serum obtained in Example 4 was taken, and the testosterone content in the serum was determined according to the method shown by the ELISA kit. The results are shown in FIG. 3. In FIG. 3, * indicates compared to the control group, *P<0.05, **P<0.01.

The testicular tissue obtained in Example 4 was weighed, physiological saline was added at a ratio of 1:9 (m/m), and the testicular tissue was broken in a tissue homogenizer to

TABLE 4

| Changes in body weight and death of rats | | | | | | | |
|---|---|---|---|---|---|---|---|
| Time (d) | 1 | 2 | 3 | 4 | 5 | 6 | 7 |
| Body weight (g) | 99.388 ± 4.89 | 106.667 ± 8.92 | 114.534 ± 10.40 | 132.340 ± 3.98 | 142.672 ± 5.68 | 153.100 ± 9.21 | 164.843 ± 17.52 |
| Death | — | — | — | — | — | — | — |

Figure 4:
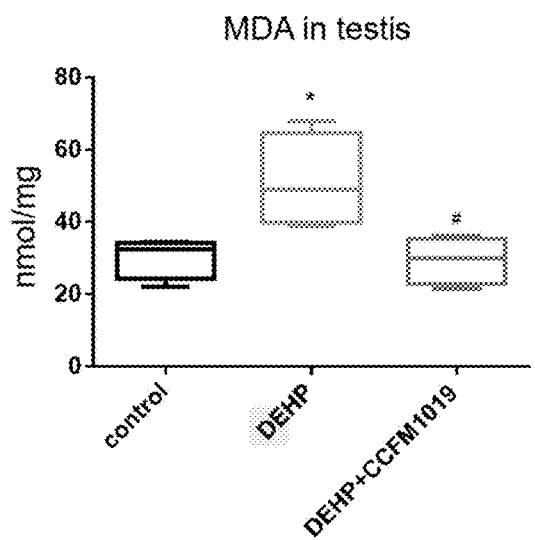
FIG. 4 is a schematic diagram showing influence of the strain of the present application on content of malondialdehyde (MDA) in testis of a DEHP exposure model rat.

Note:
— represents no rats died.

obtain 10% testicular tissue homogenate. The level of malonaldehyde (MDA) in the homogenate was determined. The determination results are shown in FIG. 4. In FIG. 4, * indicates significance compared to the control group, and # indicates significance compared to the DEHP model group; *P<0.05, #P<0.05.

Figure 5:
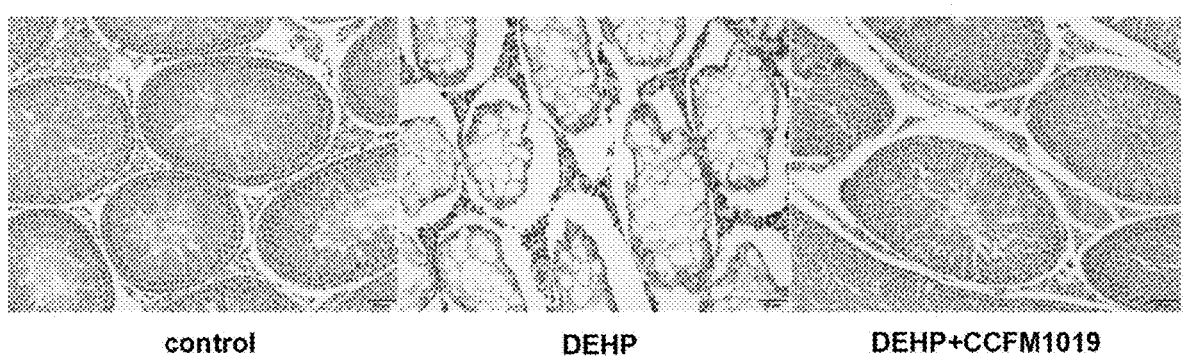
FIG. 5 is a schematic diagram showing improvement of the strain of the present application on tissue damage of testis of a DEHP exposure model rat.

Testicular tissue was taken for paraffin sectioning and conventional H&E staining was performed. The staining results are shown in FIG. 5.

By comparing the testosterone content in serum, the MDA level in the testis and the testicular pathological indexes of the DEHP exposure model group and the L. plantarum CCFM1019 intervention group, it was found that L. plantarum CCFM1019 of the disclosure can alleviate the abnormality in testosterone content in rat serum caused by DEHP intake (DEHP exposure model group: 19.65 mmol/L, CCFM1019 intervention group: 35.99 mmol/L), reduce the MDA content in the testicular tissue (DEHP exposure model group: 50.28 nmol/mg, CCFM1019 intervention group: 29.32 nmol/mg), alleviate testicular tissue damage, and play a significant role in alleviating the reproductive damage caused by DEHP intake.

Figure 6:
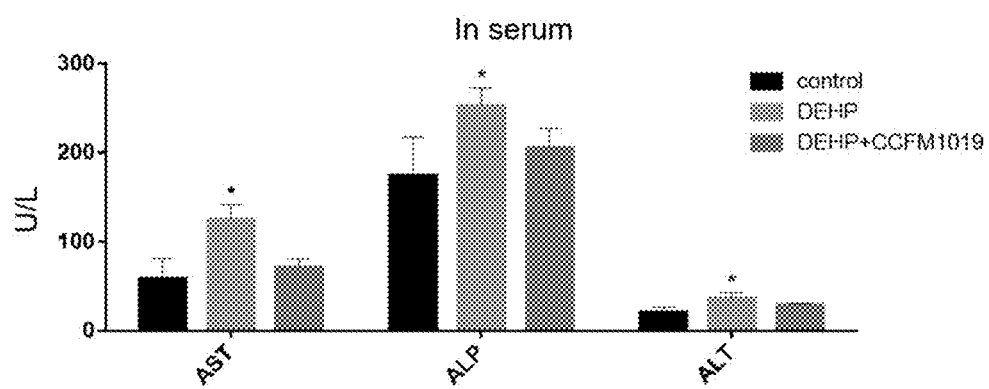
FIG. 6 is a schematic diagram showing influence of the strain of the present application on content of ALP, AST and ALT in serum of a DEHP exposure model rat.

Example 6: Improvement Effect of L. plantarum CCFM1019 on Liver Damage Indexes in Serum of DEHP-Exposed Rats The serum in Example 4 was taken to determine the blood biochemical indexes of rats, including glutamic-pyruvic transaminase (ALT), glutamic oxalacetic transaminase (AST) and alkaline phosphatase (ALP). The results are shown in FIG. 6, and in FIG. 6, * indicates significance compared to the control group; *P<0.05. By comparing the serum indexes of the DEHP exposure model group and the L. plantarum CCFM1019 intervention group, it can be seen from FIG. 6 that the L. plantarum CCFM1019 of the disclosure can effectively alleviate the abnormality in the AST, ALT and ALP indexes caused by the intake of DEHP. The content of AST in the blank control group, the DEHP exposure model group and the L. plantarum CCFM1019 intervention group was 58.35 U/L, 124.58 U/L, and 71.45 U/L, respectively; the content of ALP in the blank control group, the DEHP exposure model group and the L. plantarum CCFM1019 intervention group was 174.25 U/L, 252.60 U/L, and 205.25 U/L, respectively; and the content of ALT in the blank control group, the DEHP exposure model group and the L. plantarum CCFM1019 intervention group was 20.00 U/L, 36.74 U/L, and 28.63 U/L, respectively.

Example 7 Preparation of L. plantarum CCFM1019 Fermentation Agent

The L. plantarum CCFM1019 was inoculated into an MRS medium and cultured at 30-37° C. for at least 12 h to obtain a fermentation agent containing the L. plantarum CCFM1019.

Optionally, the bacterial cells in the fermentation solution were collected and mixed with a 3% sucrose solution to prepare a bacterial suspension.

Optionally, the bacterial suspension containing L. plantarum CCFM1019 was freeze-dried at a low temperature to prepare a L. plantarum CCFM1019 freeze-dried preparation.

Example 8 Production of Fruit and Vegetable Beverages Containing L. plantarum CCFM1019 of the Disclosure Using Same Fresh vegetables were selected, thoroughly cleaned, and juiced, and then high-temperature instant sterilization was performed. After high-temperature heat sterilization at 140° C. for 2 s, the temperature was immediately lowered to 37° C. Then the L. plantarum CCFM1019 fermentation agent prepared in the disclosure was inoculated to make the concentration reach above $10^6$ CFU/ml. The juice product was stored under refrigeration at 4° C., and thus, the fruit and vegetable beverage containing live bacteria of the L. plantarum CCFM1019 of the disclosure was obtained.

The disclosure herein can use L. plantarum CCFM1019 for fermentation to produce other fermented foods, including solid foods, liquid foods and semi-solid foods. The fermented foods include milk products, bean products, and fruit and vegetable products. The dairy products include milk, sour cream, and cheese. The fruit and vegetable products include cucumber, carrot, beet, celery, and cabbage products. The L. plantarum CCFM1019 can be resistant to gastric acid and bile salts, promote excretion of plasticizers and metabolites thereof from the body, reduce the content of the plasticizers and the metabolites thereof in serum, and significantly reduce the damage of the plasticizers and the metabolites thereof to testicular tissue and liver tissue.

The L. plantarum CCFM1019 of the disclosure has good resistance to gastric acid and bile salts, can promote excretion of the plasticizer DEHP and the metabolite MEHP thereof from the body, reduces the content of the plasticizer and the metabolite thereof in serum, and significantly reduces the damage of the plasticizer and the metabolite thereof to testicular tissue and liver tissue.

The L. plantarum CCFM1019 not only is significantly better than the intestinal resident bacteria E. coli (DEHP: 5.86%, MEHP: 0.28%) and E. faecalis (DEHP: 1.75%, MEHP: 0.17%) in terms of in vitro adsorption of DEHP and MEHP (52.22% and 70.54% respectively), but also is better than the commercial strain L. rhamnosus LGG (DEHP: 13.75%, MEHP: 15.60%). In the bodies of rats, L. plantarum CCFM1019 can significantly reduce the DEHP and MEHP content in serum (by 54.3% and 55.7% respectively compared to the blank control group), and at the same time increase the DEHP and MEHP content in feces (by 34.18% and 93.88% respectively compared to the blank control group). Therefore, the L. plantarum CCFM1019 of the disclosure can be used as an effective means to prevent and alleviate body damage caused by DEHP and MEHP, and has no toxic side effects of drugs. The L. plantarum CCFM1019 can be used to prepare pharmaceutical compositions and fermented foods for alleviating and preventing the toxicity of DEHP and the metabolites thereof, and has a very broad application prospect.

Although the disclosure herein has been disclosed above in the preferred embodiments, it is not intended to limit the disclosure herein. Anyone familiar with this art can make various changes and modifications without departing from the spirit and scope of the disclosure. Therefore, the protection scope of the disclosure should be defined by the claims.

What is claimed is:

1. A method of preparing a pharmaceutical composition or a fermented food or beverage product, said method comprising using a microbial preparation comprising >$10^6$ CFU/mL of isolated live Lactobacillus plantarum (L. plantarum) CCFM1019 deposited on 11 Feb. 2018 at the Guangdong Microbial Culture Collection Center (GDMCC), Guangdong Institute of Microbiology, Guangzhou, with the accession number GDMCC 60333.

2. The method of claim 1, wherein the L. plantarum CCFM1019 is resistant to gastric acid and bile salts.

3. The method of claim 1, wherein the *L. plantarum* CCFM1019 has the capacity to adsorb bis(2-ethyl hexyl) phthalate (DEHP) plasticizer, mono(2-ethyl hexyl) phthalate (MEHP) plasticizer, and metabolites thereof and to promote fecal excretion of DEHP and MEHP plasticizers and metabolites thereof.

4. The method of claim 1, wherein the microbial preparation is a bacterial suspension comprising the *L. plantarum* CCFM1019 and a sucrose solution.

5. The method of claim 1, wherein the fermented food or beverage product is a solid food, a liquid food, or a semi-solid food.

6. The method of claim 1, wherein the fermented food or beverage product is a dairy product, bean product, fruit product, or vegetable product.

7. The method of claim 6, wherein the dairy product comprises milk, sour cream, or cheese.

8. The method of claim 6, wherein the vegetable product comprises cucumber, carrot, beet, celery, or cabbage.

\* \* \* \* \*